United States Patent
Jardret et al.

(10) Patent No.: US 6,945,097 B2
(45) Date of Patent: Sep. 20, 2005

(54) CHARACTERISTIC STRAIN AND FRACTURE RESISTANCE FOR SCRATCH INDEPENDENTLY OF INDENTER GEOMETRY

(75) Inventors: Vincent P. Jardret, Knoxville, TN (US); Pierre Jean Morel, Knoxville, TN (US)

(73) Assignee: MTS Systems Corporation, Eden Prairie, MN (US)

(*) Notice: Subject to any disclaimer, the term of this patent is extended or adjusted under 35 U.S.C. 154(b) by 0 days.

(21) Appl. No.: 10/409,656

(22) Filed: Apr. 8, 2003

(65) Prior Publication Data

US 2004/0011119 A1 Jan. 22, 2004

Related U.S. Application Data

(60) Provisional application No. 60/374,856, filed on Apr. 11, 2002, and provisional application No. 60/372,516, filed on Apr. 10, 2002.

(51) Int. Cl.[7] ............................................. G01N 3/46
(52) U.S. Cl. ........................... 73/81; 73/85; 73/799; 73/806; 73/81
(58) Field of Search .............................. 73/81, 82, 85, 73/760, 781, 788, 789, 790, 799, 806, 818, 821, 822

(56) References Cited

U.S. PATENT DOCUMENTS

| | | | | |
|---|---|---|---|---|
| 2,801,540 A | * | 8/1957 | Rondeau | .................... 73/150 R |
| 3,021,707 A | * | 2/1962 | Haueisen | .................. 73/150 R |
| 4,791,807 A | * | 12/1988 | Oechsle | ......................... 73/78 |

(Continued)

FOREIGN PATENT DOCUMENTS

| | | | | |
|---|---|---|---|---|
| GB | 2146129 A | * | 4/1985 | ............ G01N/3/46 |
| JP | 62245131 A | * | 10/1987 | ............ G01N/3/00 |
| JP | 63015139 A | * | 1/1988 | ............ G01N/3/46 |
| JP | 402095239 A | | 4/1990 | ..................... 73/81 |

OTHER PUBLICATIONS

Vaughn et al., "Scratch Indentation, A Simple Adhesion Test Method for Thin Films on Polymeric Supports", VSP, Adhesion Measurement of Films and Coatings, 1995, pp. 127–142.*

Kattamis, T. Z., "On the Evaluation of Adhesion of Coatings by Automatic Scratch Testing", VSP, Adhesion Measurement of Films and Coatings, 1995, pp. 143–160.*

Venkatarama et al., "Continuous Microscratch Measurements of Thin Film Adhesion Strengths", VSP, Adhesion Measurement of Films and Coatings, 1995, pp. 161–174.*

Sarin, V. K., "Micro-scratch Test for Adhesion Evaluation of Thin Films", VSP, Adhesion Measurement of Films and Coatings, 1995, pp. 175–188.*

Fischer–Cripps, A. C., "Nanoindentation", CSIRO, 2000, pp. 1–24.*

Fischer–Cripps, A. C., "Introduction to UMIS II", CSIRO, 2000, pp. 1–31.*

(Continued)

Primary Examiner—Hezron Williams
Assistant Examiner—David A. Rogers
(74) Attorney, Agent, or Firm—Westman, Champlin and Kelly, PA

(57) ABSTRACT

The invention involves an apparatus and method for calculating characteristics of materials, such as equivalent strain, using an indenter where the method used is independent of indenter geometry. The method includes performing a scratch test to calculate the strain for each of a plurality of indenter shapes, such as a theoretical sphere and cone, using known equations. The strain of a composite indenter, such as a cone with a rounded tip, can then be determined taking into account contributions from each of the plurality of theoretical shapes.

14 Claims, 16 Drawing Sheets

U.S. PATENT DOCUMENTS

| | | | | |
|---|---|---|---|---|
| 4,852,397 A | | 8/1989 | Haggag | 73/82 |
| 4,856,326 A | * | 8/1989 | Tsukamoto | 73/150 A |
| 4,984,453 A | * | 1/1991 | Enomoto | 73/81 |
| 5,027,650 A | * | 7/1991 | Oblas et al. | 73/150 A |
| 5,067,346 A | * | 11/1991 | Field | 73/81 |
| 5,359,879 A | * | 11/1994 | Oliver et al. | 73/7 |
| 5,490,416 A | * | 2/1996 | Adler | 73/82 |
| 5,546,797 A | * | 8/1996 | Dutta et al. | 73/150 A |
| 5,553,486 A | * | 9/1996 | Bonin | 73/105 |
| 5,696,327 A | * | 12/1997 | Huang et al. | 73/845 |
| 5,866,807 A | * | 2/1999 | Elings et al. | 73/105 |
| 5,965,896 A | * | 10/1999 | Marton | 250/559.4 |
| 6,053,034 A | * | 4/2000 | Tsui et al. | 73/81 |
| 6,339,958 B1 | | 1/2002 | Tsui et al. | 73/150 |
| 6,343,502 B1 | * | 2/2002 | Subhash et al. | 73/81 |
| 6,502,455 B1 | * | 1/2003 | Gitis et al. | 73/150 A |
| 6,520,004 B1 | * | 2/2003 | Lin | 73/81 |
| 2002/0104371 A1 | * | 8/2002 | Gitis et al. | 73/81 |

OTHER PUBLICATIONS

Briscoe, B.J., "Isolated contact stress deformations of polymers; the basis for interpreting polymer tribology". New Directions in Tribology, Plenary and Invited Papers from the World Tribology Congress, $1^{st}$, London, Sep. 8–12, 1997. pp. 191–196.

Bucaille, J.L. et al. "Finite–element analysis of deformation during indentation and scratch tests on elastic–perfectly plastic materials". Philosophical Magazine A (Phys Conden Matt) vol. 82 (10), Jul. 10, 2002, pp. 2003–2012.

Gauthier, C. et al. Viscoelastic–viscoplastic analysis of a scratching and sliding single contact on a polymer surface. Euromat 2000 Conf Adv Mech Behav Plast Dam 2000, pp. 213–218.

Gauthier, C. et al. "Elastic recovery of a scratch in a polymeric surface: experiments and analysis". Tribology International vol. 34 (2001) pp. 469–479.

Jardret, V.D. et al. "Understanding and quantification of elastic and plastic deformation during a scratch test". Wear vol. 218 (1), Jun. 15, 1998, pp. 8–14.

Jardret, V.D. et al. "On the robustness of scratch testing for thin films: the issue of tip geometry for critical load measurement". Mechanical Properties VIII, MRS Symp Proc vol 594, 2000, pp. 395–400.

Mutoh, Y. et al. "On evaluation of adhesive strength in scratch test of coating materials". (English abstract) Transactions of the Japan Society of Mechanical Engineers vol. 68(6), Jun. 2002, pp. 909–915.

Randall, N.X. et al. "The effect of intrinsic parameters on the critical load as measured with the scratch test method". Surface and Coatings Technology vol. 137(2), Mar. 15, 2001, pp. 146–151.

Szudrowicz, M. "About the mechanism of coatings damage during the scratch test". (English abstract) Tribologia vol. 31 (4), 2000, pp. 723–730.

Xiaoyu, J. et al. "Frictional contact analysis of scratch test for elastic and elastic–plastic thin–coating/substrate materials". Thin Solid Films vol. 414 (1), Jul. 2002, pp. 63–71.

Xie, Y. et al. "A controlled scratch test for measuring the elastic property, yield stress and contact stress–strain relationship of a surface". Surface Coatings and Technology vol. 27 (2–3), May 22, 2000, pp. 130–137.

T.W. Wu, "Microscratch and load relaxation tests for ultra–thin films", J. Mater. Res., vol. 6, No. 2, pp. 407–426, Feb. 1991. XP002900499.

Park et al., "An energy approach to quantification of adhesion strength from critical loads in scratch tests", Thin Solid Films, Elsevier–Sequoia S.A. Lausanne, CH, vol. 307, No. 1–2, pp. 156–162, Oct. 10, 1997. XP004109332.

* cited by examiner

CHARACTERISTIC STRAIN AND FRACTURE RESISTANCE FOR SCRATCH INDEPENDENTLY OF INDENTER GEOMETRY

CROSS REFERENCE TO RELATED APPLICATIONS

This application claims the benefit of U.S. provisional patent application 60/372,516, filed Apr. 10, 2002 and 60/374,856 filed Apr. 11, 2002, the contents of which are both incorporated herein by reference.

BACKGROUND OF THE INVENTION

The scratch resistance of polymers has been the subject of numerous studies that have led to the characterization of plastic and fracture phenomena during scratching. Viscoelastic and viscoplastic behavior during scratching have been related to dynamic mechanical properties that can be measured via dynamic nano-indentation testing. Yet, an understanding of the origin of the fracture phenomena in a polymer, such as poly-methylmethacrylate(PMMA), during scratching remains approximate. Parameters like tip geometry and size, scratch velocity and loading rate, and applied strain and strain rates, have been considered critical parameters for the fracture process, but no correlation has been clearly established.

Perhaps the oldest way for measuring the hardness of a material is based on a scratch test. Mineralogists first developed this kind of testing to evaluate the hardness of stones. The hardness scale that resulted from this work was based on the ability of one material to scratch or to be scratched by another. The scratch test has also been found to have applications in understanding the fundamental mechanisms of wear adhesion. Scratching, abrasion, and wear are all factors that diminish the properties of a surface.

In recent years the mechanical properties of polymers have been studied. Polymer materials are useful as surface coatings due to low cost and because they can be formed or molded easily. Nevertheless, their useful life is often limited by poor mechanical properties. For example, automotive paints are subject to numerous forms of degradation. In particular, scratching and abrasion cause degradation of appearance and loss of optical performance of these materials.

In view of the foregoing, any improvements in scratch testing would be beneficial.

SUMMARY OF THE INVENTION

The invention involves an apparatus and method for calculating characteristics of materials, such as equivalent strain, using a scratch tip or indenter where the method used is independent of indenter geometry. The method includes performing a scratch test to calculate the strain for each of a plurality of indenter shapes, such as a theoretical sphere and cone, using known equations. The strain of a composite indenter, such as a cone with a rounded tip, can then be determined taking into account contributions from each of the plurality of theoretical shapes.

In one embodiment, method of determining critical properties of an unknown test material by scratch testing, comprises the steps of applying a load over a surface of a test sample using a scratch tip having selected geometric parameters at a selected speed to form a groove; measuring a critical depth of the groove and the critical load applied; approximating a critical strain of the test sample as a function of the geometric parameters, the critical depth and the critical load.

In another embodiment, a scratch indenter apparatus comprises a scratch tip of selected geometric parameters moving at a selected speed over a test sample; an electromagnetic device capable of applying a variable load to the moving scratch tip to form a groove in the test sample; a sensor measuring a critical depth of the groove and the critical load applied; and circuitry operably coupled to the sensor to approximate a critical strain of the test sample as a function of the geometric parameters, the critical depth and the critical load.

The scratch resistance of polymers has been the subject of numerous studies that have led to the characterization of plastic and fracture phenomena during scratching. Viscoelastic and viscoplastic behavior during scratching have been related to dynamic mechanical properties that can be measured via dynamic nano-indentation testing. Yet, an understanding of the origin of the fracture phenomena in a polymer, such as poly-methylmethacrylate(PMMA), during scratching remains approximate. Parameters like tip geometry and size, scratch velocity and loading rate, and applied strain and strain rates, have been considered critical parameters for the fracture process, but no correlation has been clearly established.

Fracture in scratch testing is modeled as resulting from tensile stresses behind the scratch tip. A new scratch fracture parameter is in introduced that is related only to material properties and not to the scratch tip geometry. These methods bring a new understanding to the origin of fracture mechanism during scratch testing, and the influence of indentation strain on the fracture strength of materials.

DETAILED DESCRIPTION OF THE ILLUSTRATIVE EMBODIMENTS

Wear problems in materials are notoriously difficult to quantify. Scratching can be defined as the deformation and damage caused by the motion of a sharp object, the "scratch tip", in contact with a surface. The scratch can be used as a model for two types of real situations. The first is a single scratch on a surface. This would be the equivalent of a sand grain scratching automotive paint, a key scratching a car, or a particle of dust scratching the lens of a camera. In these cases, the scratch tip represents only one asperity, which slides on the surface with a load applied to it to cause the scratch.

The second situation that can be modeled by scratch testing is complex wear problems, such as a spinning brush used in typical automatic car washes, in which there are multiple points of contact or asperities applied to the surface of a car. For this situation, the scratch tip represents a simplification of the complex abrasive situation. In this case, the scratch test represents only one asperity rather than the complex effect of all of the asperities involved in the real contact. Ideally, the results of the scratch test are generalized to understand the larger complex abrasion problem. In both single scratch and complex wear situations, the scratch process generates deformation on the surface, which can be classified as elastic, plastic, fracture and delamination, or combinations of these.

In one scratch test, a scratch tip slides along a surface of a test material with a normal load applied. Important parameters about the test material can be derived from such a test from the deformation and damage caused by the scratching. However, several parameters particularly related to the geometry of the contact and kinetics between scratch tip and surface will influence scratch test results.

Figure 1:
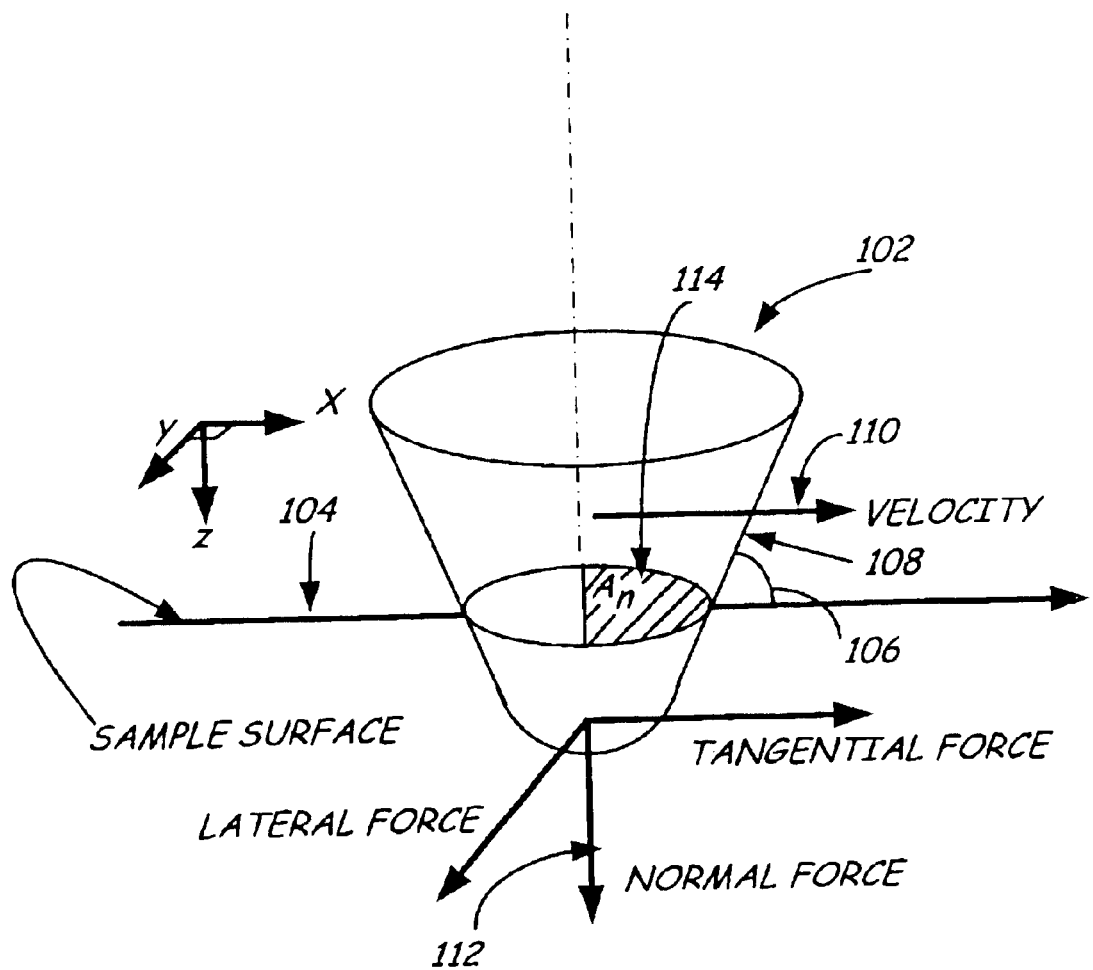
FIG. 1 is a schematic illustration of a scratch tip moving along the surface of a test material sample.

FIG. 1 is a schematic drawing of a scratch tip moving along sample surface 104 of a test material. The geometry of scratch tip 102 is one parameter that is of primary importance in the scratch process. Scratch tip 102 can have many different shapes. These shapes reproduce approximately all of the possible geometries that an asperity can have in a real contact. A non-exhaustive list of the shapes would be conical, pyramidal (Berkovich, Vickers, cube corner), spherical and flat punch, and combinations of these.

The geometry of scratch tip 102 has an important effect on the type of deformation and stresses induced in the test material. For example, the edges of the pyramidal shapes generate a concentration of stress at these geometrical singularities. Thus, the Berkovich tip will generate a stress field quite different than a sphere, due to the presence of the edges, which act like a knife. The flow of the material in front of the scratch tip is different for a cone and a pyramid. For the cone, the material does not meet a discontinuity in the surface geometry, whereas for the pyramid, material flows along one surface until it finds an edge where the characteristics of the flow change. Furthermore, for the pyramidal shape, the scratch behavior is different when the scratch tip moves in an edge or face forward. In these two extreme cases, the deformation is different due to a different stress field. In a brittle or semi brittle material, the presence of edges has a strong influence on the fracture because of the stress concentrations they generate.

The attack angle 106 is another important parameter and is defined as the angle between the test material surface 104 and scratch tip surface 108. Attack angle 106, like the scratch tip shape, has an important influence on the type of deformation and damage caused to the surface 104. The smaller the attack angle, the less severe the abrasive contact. If the attack angle becomes too large, the deformation changes into a cutting behavior and the test material is shaved off the test material and slides up the surface 108 of scratch tip 102.

The continuum of elastic, ductile and brittle test material responses during scratch testing have been studied. Cutting behavior is triggered by a critical value of attack angle 106 or a cutting angle. In the present inventions, the attack angle 106 can generally be kept smaller than the cutting angle.

In the case of a sphere sliding on a surface, the attack angle is not constant if the load is increased as the scratch is made. At the point of first contact between the sphere and the surface the attack angle is very small. As the sphere penetrates into the test material surface, the attack angle gradually increases. The attack angle can equal 0° initially and reach 900 when half of the sphere penetrates into the material. The varying attack angle strongly influences the strain induced in the material by the scratch tip.

Another important test parameter is the speed of the scratch tip on the surface. The velocity 110 of scratch tip 102 controls the velocity of material flow around scratch tip 102 and the level of the local stresses for a strain rate sensitive material. The scratch tip's velocity is directly related to the strain rate induced in the material. For conical and pyramidal scratch tip indenters, an increase in the scratch tip velocity or speed generates a proportional increase in the strain rate. In the case of polymers and time-temperature dependent materials, a high scratch tip speed inducing a high strain rate will dramatically change the test material response.

A scratch experiment can generate many kinds of deterioration behavior and damage, which require different parameters to describe. The scratch deterioration behaviors are often categorized as follows: elastic-plastic behavior, visco-elastic, visco-plastic, fracture behavior. Elastic deformation is reversible and is recovered behind the scratch tip. Plastic plowing is permanent deformation that can be observed afterwards by making a cross sectional profile of the scratch.

Figure 2:
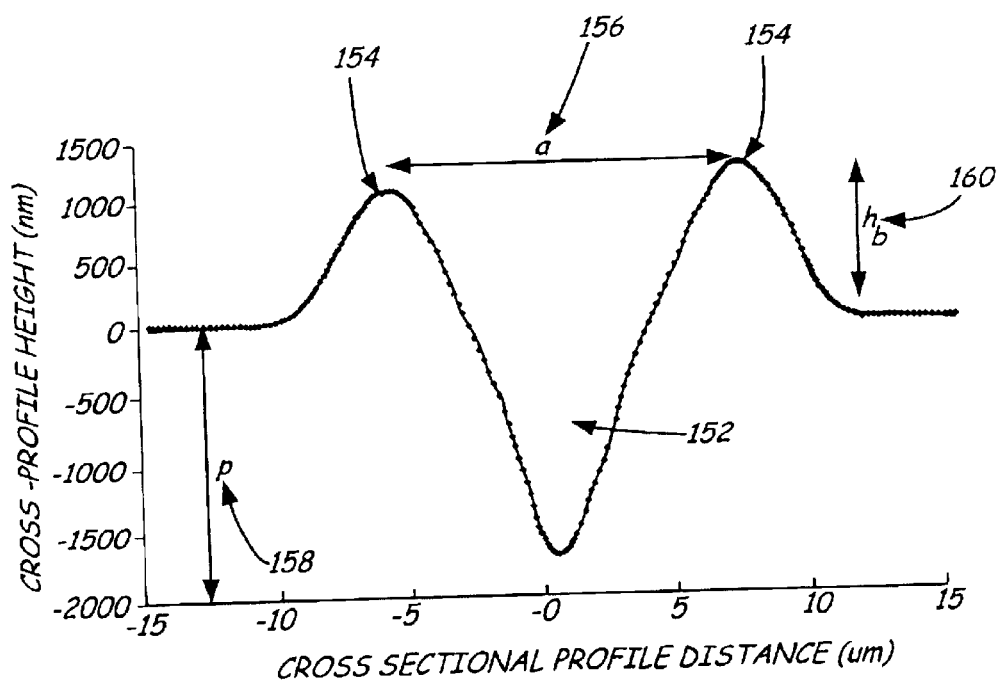
FIG. 2 is a schematic illustration of a cross-sectional profile of a groove formed during a scratch test with cross-section parameters.

FIG. 2 show results of a scratch test performed at 100° C. on PMMA and 30 mN load having a groove caused by plastic deformation. The scratch test results in produces a groove with cross section 152 flanked by two lateral pile-ups 154. Plastically deformed scratch grooves or tracks can be described by the following parameters: scratch width a is the distance between the peaks of the pile-up on each side of the groove and is indicated at 156; scratch residual depth p is the height between the nominal surface and the bottom of the groove and is indicated at 158; and scratch pile-up height $h_b$ is the height of the peak of the pile-up above the nominal surface and is indicated at 160; and projected contact area described below. The scratch hardness $H_s$ has been defined as:

$$H_S = \frac{F_N}{A_n} \quad \text{Equation 1}$$

where $F_N$ is the normal force 112 applied to surface 104 (shown in FIG. 1) and $A_N$ is the projected contact area indicated as 114 on FIG. 1. The scratch hardness does not take the friction into account. The transition between elastic and plastic deformation during scratch testing can be used to determine the yield stress of the material. The simultaneous occurrence of these two types of deformation influences the projection contact area between scratch tip 102 and test material surface 104. The cross sectional area of the scratch tip in contact with the material at the nominal surface, is defined as the projected contact area $A_n$.

Consider a scratch tip that has a spherical shape. If the contact is fully elastic, the contact area will be a full circle that recovers entirely behind the scratch tip. For a fully plastic contact, the material is permanently deformed and the area of contact will be a half circle with area $A_N$ indicated as 114 on FIG. 1 given by:

$$A_N = \frac{1}{2}\pi\frac{a^2}{4} \quad \text{Equation 2}$$

where a is scratch width 156. However, if both elastic and plastic deformation develops between scratch tip 102 and test material surface 104, the contact area is modified due to the elastic recovery behind the scratch tip. The projected contact area is a parameter in scratch testing.

Critical load is parameter in scratch testing. In addition to elastic and plastic deterioration, scratching can also produce fracture. Fracture occurs when the material cannot support the stresses generated by the scratch tip. The value of normal load or force 112 applied to scratch tip 102 at which the fracture occurs is called the critical load. The critical load is often used as a measure of the fracture resistance during scratching.

Fracture can primarily result from parameters such as scratch tip velocity 110 or speed, attack angle 106, and the scratch tip geometry.

Figure 3:
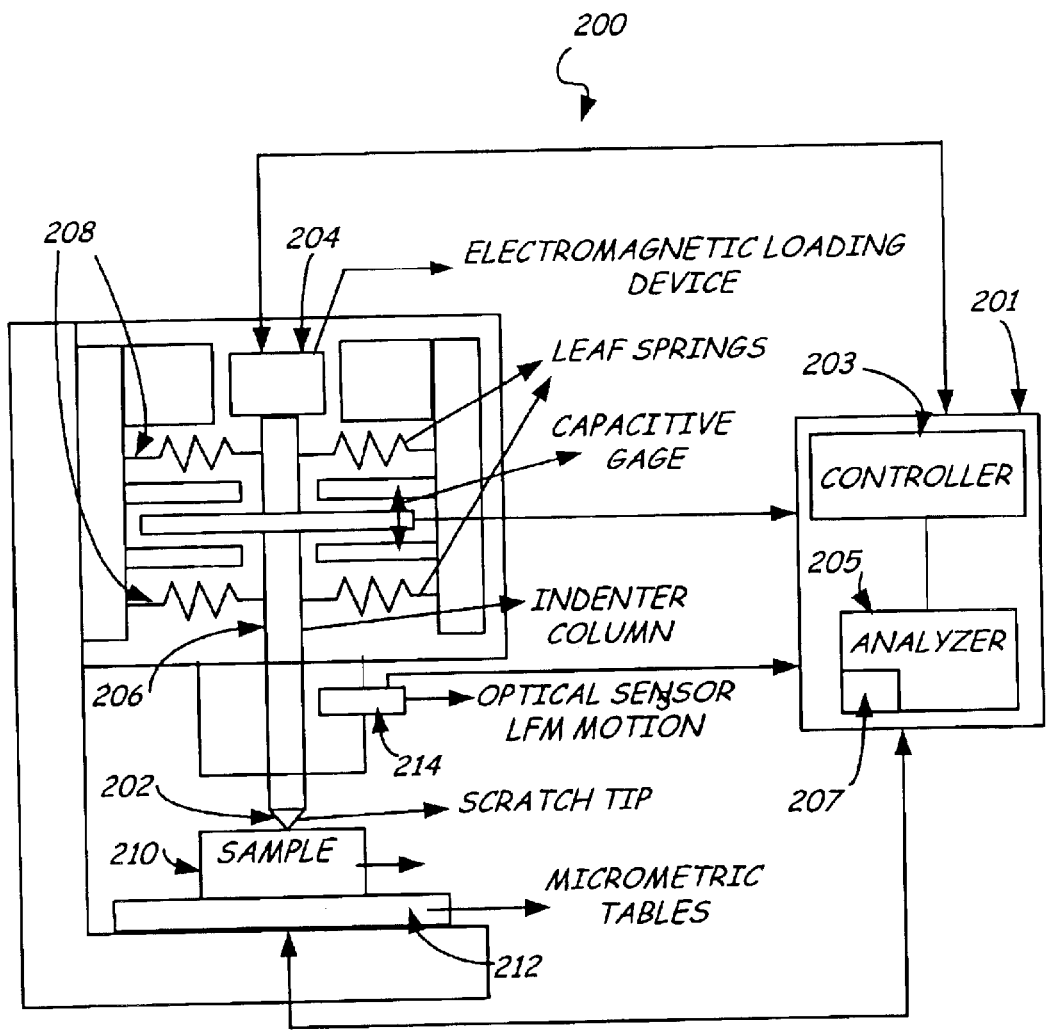
FIG. 3 is a schematic diagram of an apparatus used to carry out some methods of the present inventions.

FIG. 3 is a schematic diagram of an apparatus that can be used to carry out the methods of the present invention. Scratch apparatus 200 can be an indenter apparatus known as a Nano Indenter XP® manufactured by MTS System Corporation of Eden Prairie, Minn. It was originally developed for depth sensing indentation, but can be configured for scratch testing experiments. The Nano Indenter XP® is described in U.S. Pat. No. 4,848,141 which is herein incorporated by reference. The Nano Identer XP head is load-controlled by circuitry 201 comprising controller 203 controlling electromagnetic load device 204 having a magnet/coil system in a direction normal to the sample surface. Electromagnetic device 204 allows for great precision and rapid control of the load. The scratch tip 202 is located at the bottom of column 206 held in position by leaf springs 208 to provide very low vertical stiffness and high lateral stiffness to restrain lateral motion of column 206. Circuitry 201 further comprises analyzer 205 for analyzing test results. Storage medium 207 can be included for storing instructions for performing scratch tests of the present inventions including analyzing test results and storing test data. Storage medium 207 can also store geometric parameters for various scratch tips or indenters. As appreciated by those skilled in the art, the controller 203 and analyzer 205 can comprise separate devices.

The maximum vertical displacement of column 206 is 1.5 mm and the maximum applied load is 500 mN for the standard system. The test material sample 210 is fixed on a sample tray that can be moved with micrometric tables 212 controlled by controller 203 to provide high positioning precision in both horizontal orthogonal directions.

Apparatus specifications are given in Table 1 and Table 2.

TABLE 1

| Indentation Specifications for the Nano Indenter XP | |
|---|---|
| Normal maximum load | 500 mN |
| Normal force resolution: | 50 nN |
| Maximum indentation depth: | 1 mm |
| Displacement resolution: | <0.02 nm |

TABLE 2

| Scratch test specifications for the Nano Indenter XP | |
|---|---|
| Scratch speed: | 0.1 µ/s → to 2.5 mm/s |
| Scratch length: | 10 µm → to 100 mm |
| Maximum lateral force: | 250 mN (All direction) |
| Lateral force resolution: | 2 µN |
| Lateral force Noise level: | <500 µN (without contact) |
| Scratch orientation: | 0° to 360° |

The dynamic properties of the materials can be measured by indentation using the Continuous Stiffness Measurement (CSM) option. The principle of the CSM is to add a small amplitude oscillation to the continuous load signal. Analysis of the signal in relation to the signal coming from the displacement of the tip gives the dynamic stiffness, S and the contact damping, D, as a function of the penetration into the test material surface. These dynamic measurements allow the calculation of the loss modulus E", storage modulus E', and tangent δ, using the following equations:

$$E' = \frac{\sqrt{\pi}}{2}\frac{S}{\sqrt{A}} \quad \text{Equation 3}$$

$$E'' = \frac{\sqrt{\pi}}{2}\frac{D\omega}{\sqrt{A}} \quad \text{Equation 4}$$

$$\tan\delta = \frac{E''}{E'} \quad \text{Equation 5}$$

$$H = \frac{P}{A} \quad \text{Equation 6}$$

where S is the dynamic stiffness of contact, D is the contact damping, ω is the angular frequency of the oscillation, A is the area of contact during indentation and is generally equal to the cross-sectional area of a circle with for a conical tip or twice the area of $A_N$ shown in FIG. 1, H is the indentation hardness and P is the load. The strain rate applied during indentation has been defined when the hardness is constant as:

$$\dot{\varepsilon} = \frac{\dot{h}}{h} = \frac{1}{2}\frac{\dot{P}}{P} \quad \text{Equation 7}$$

where P is the load and h the indenter penetration. Some indentation tests in the present invention were performed at a constant value of $$\frac{\dot{P}}{P} = 0.1.$$

nm·nm$^{-1}$·sec$^{-1}$.

The entire Nano Indenter XP can be installed in a temperature chamber to perform tests at a selected temperature.

Temperature can be controlled in the chamber with a precision of 0.1° C. over the range of operation (−50° C. to 100° C.). Before and after each test (indentation or scratch), the temperature of the chamber is recorded. The temperature is adjusted before starting a new test and the temperature regulation system is turned off to avoid any noise or vibration during the experiment.

Figure 4:
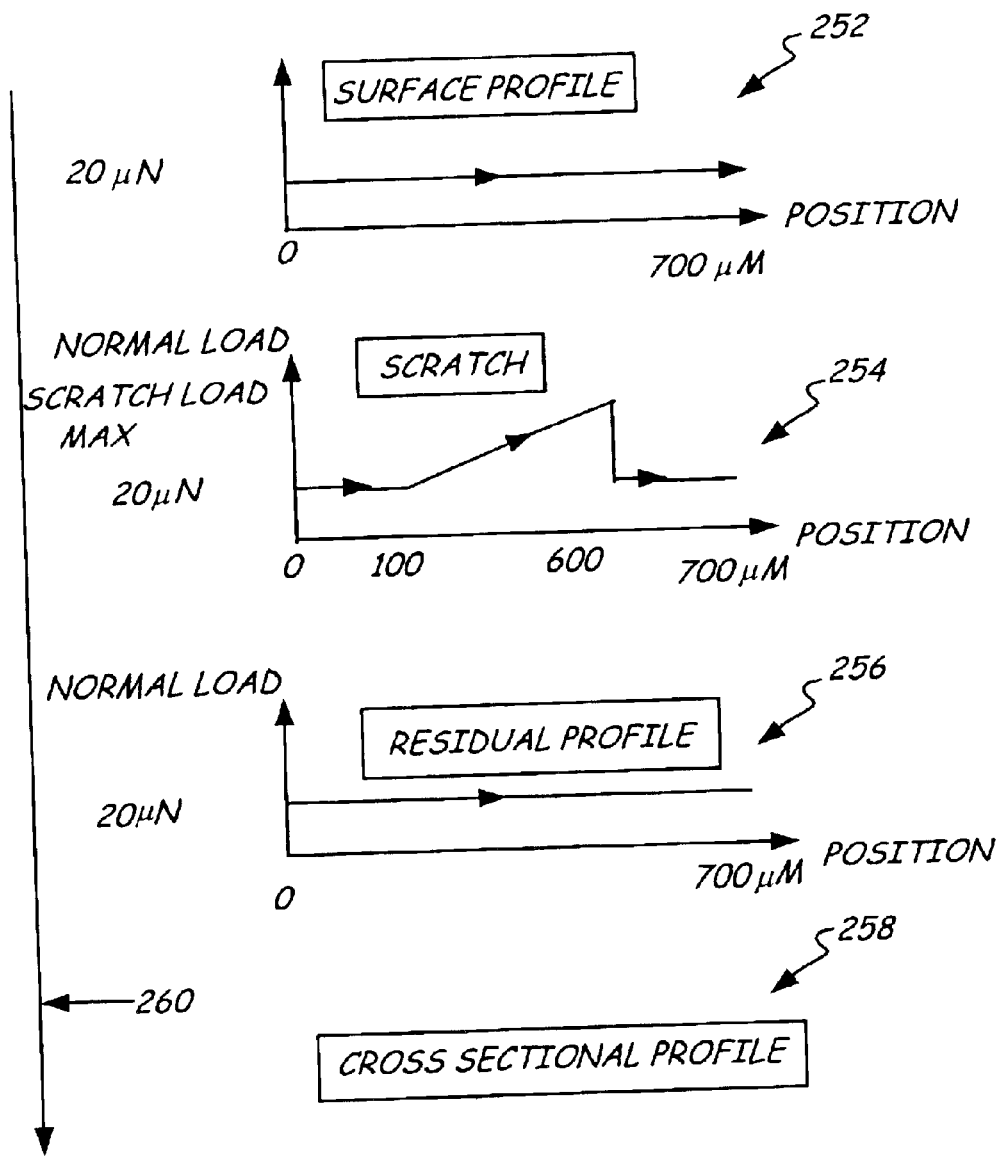
FIG. 4 is a diagram of scratch test steps used in some methods of the present inventions.

Scratch tests were performed by moving micrometric tables 212 that carry sample 210 while the indentation head controls the load applied to the surface of the sample 210 via scratch tip 202. During a scratch test, the normal force applied to the sample can be held constant, increased, or decreased. FIG. 4 schematically illustrates the steps of a typical scratch test comprising four steps 252, 254, 256, 258. Step order is indicated by arrow 260.

At step 252, a very small normal load (20 $\mu$N) is applied as scratch tip 202 (shown in FIG. 3) is moved along a path to profile the surface of sample 210 in order to record the original morphology of the surface before scratching.

At step 254, the normal load is increased linearly from 20 $\mu$N to the maximum load to create the scratch as scratch tip 202 is moved along the same path.

At step 256, post scratch profile was performed along the same path, under a very small load (20 $\mu$N), to measure the residual deformation in the groove formed from the scratch test.

Finally, at step 258, a profile across the scratch groove was performed to measure the shape of the groove and extent of plastic deformation. The equivalence of the contact pressure in a scratch test and hardness in indentation test is known. Also, it is known that for polymers an increase in hardness occurs when the strain rate is increased for room temperature scratching.

The strain rate in a scratch test can be defined as:

$$\dot{\varepsilon}_s = \frac{V_{tip}}{a} \quad \text{Equation 8}$$

where $V_{tip}$ is the scratch speed or velocity and a is the scratch width.

In an indentation test, the hardness is defined as:

$$H = \frac{P_m}{A} \quad \text{Equation 9}$$

where P is the maximum load and A the area of contact.

For the scratch test the contact pressure, or scratch hardness, is estimated by:

$$H_s = q\frac{4F_n}{\pi a^2} \quad \text{Equation 10}$$

where $F_n$ is the normal load, a is the residual scratch width, and q is a material coefficient equal to one in this study of PMMA.

The Lateral Force Measurement (LFM) option of the Nano Indenter XP indicated at 214 allows the measurement of the forces in the X-Y horizontal plane. During a scratch test these forces correspond to tangential friction force and lateral scratch force. These forces are obtained by measuring optically the lateral displacement of the indenter column in two orthogonal directions (X and Y). The lateral force applied to the column can be calculated from the lateral stiffness of the column assembly and the lateral displacement.

Due to the small size of the scratch tip, it is difficult to manufacture certain geometrical shapes like a cone without some rounding at the tip. For this reason, conical tips are normally defined by the included angle of the cone a, and the estimated radius of the tip rounding R.

Figure 5:
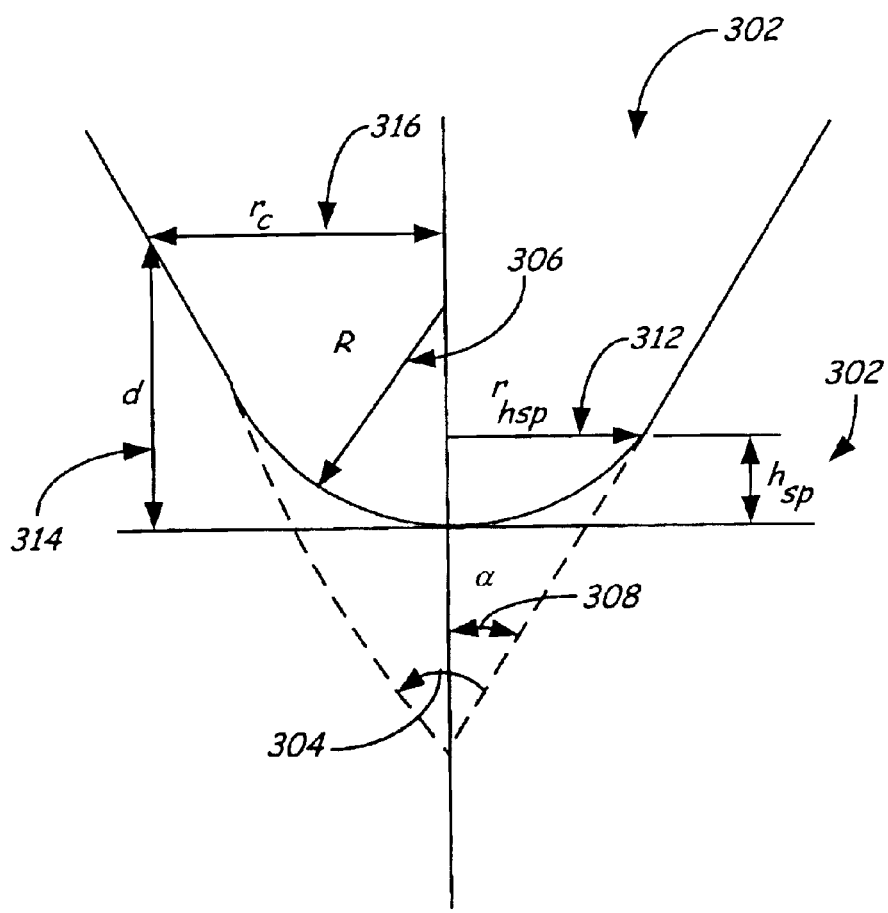
FIG. 5 is a schematic diagram of a blunted conical scratch tip with geometric parameter.

FIG. 5 shows a rounded cone-shaped scratch tip showing various parameters and can be used to carry out methods of the present invention. In order to characterize precisely the shape of the scratch tip indentation tests were conducted on a material for which the elastic modulus is well known. Fused silica is commonly used for this purpose. The spherical part of the scratch tip can be characterized by the equivalent indenter width, or contact radius, compared to the indenter height. The measurement of the elastic contact stiffness as a function of contact depth describes the scratch tip.

It is known that the modulus E of a material is a function of the contact stiffness S and the contact area A and is given by:

$$E = \frac{\sqrt{\pi}}{2}\frac{S}{\sqrt{A}} \quad \text{Equation 11}$$

From this relation, and assuming that the contact area is a circle in the case of a conical indenter, the radius of contact $r_c$ can be expressed:

$$r_c = \frac{S}{2E} \quad \text{Equation 12}$$

The radius can be plotted as a function of depth to obtain the shape of the tip.

As defined previously, the critical load is that at which the material starts to fracture. During experiments, the load is increased linearly and its value is recorded as a function of the distance along the scratch path. The value of the critical load is determined by analyzing data after the test. When particles are chipped out of the surface and/or cracks appear in and/or outside the scratch, there is a sudden movement of the scratch tip that can be seen as irregularities in the scratch penetration, and tangential force curves in the residual scratch morphology.

The critical load value is determined at the point showing the first indications of irregularities or fracture. The critical load value can also be confirmed by an optical observation of the scratch track and a length measurement along the scratch track.

Scratch tip shape or geometry influences critical load values because geometry as well as attack angle are parameters that play an important role in determining the stresses applied to the material and resulting fracture. Additionally, as mentioned previously the shape of the fracture is also can be an important parameter by providing useful information about what caused the fracture.

Polymers exhibit a transition in mechanical behavior around their glass transition temperature. In order to observe a change in behavior in the range of temperatures available for indentation and scratch tests, the polymer material must have a transition in the range of temperature available to the Nano Indenter XP in the heat chamber (between 0° C. and 100° C.). PMMA (poly-methylmethacrylate), an amorphous thermoplastic, has a transition close to this range (around 110° C.), and is glassy at room temperature. Furthermore, numerous studies on this material have provided a great deal of information on its visco-elastic properties, the loss and storage moduli and the stress/strain behavior as a function of temperature.

Indentation tests provided basic information on the elastic moduli and hardness as a function of temperature. The loss and storage moduli, the hardness, and tan δ are obtained using CSM data and the equations are presented above. A Berkovich indenter was used for the indentation tests, which were performed between 5° C. and 90° C.

Generally, there can be a decrease in the storage modulus and hardness as the temperature is increased. Over the same range of temperature, the loss modulus increases slightly, which leads to an increase in tan δ. The combined observations indicates that the glass transition would be at higher temperature. For PMMA, the glass transition is at 100° C. at 1 Hz given by dynamic mechanical testing (DMA). The storage modulus obtained with indentation test at room temperature (5 Gpa) is higher than the values given by DMA testing at 1 Hz, which is known.

Since the scratch resistance is mainly determined by plastic deformation and fracture behavior, differences between ductile and brittle behavior in the scratch test can be characterized by several important parameters. Ductile deformation during scratching is evaluated through the contact pressure, the residual groove depth, and the height of the pile-up. The critical load, which is the applied load where fracture first occurs is the basic measure of the fracture resistance.

The indentation tests were conducted with a Berkovich indenter and the scratch tests with a 90° cone with a 2 μm radius tip. Referring back to FIG. 5, scratch tip 302 has an angle 304 and radius R indicated as 306. Results for maximum load and contact area were used to calculate indentation hardness using Equation 9. Results for critical load and scratch width were used to compute scratch hardness using Equation 10.

The difference in value between the indentation hardness and the scratch hardness is due to the difference in strain rate between the two different experiments. Plastic deformation during scratch testing is commonly measured by the pile-up height and the residual depth of the scratch shown in FIG. 2. The plastic deformation produced during indentation testing and scratch testing depends on the relative magnitude of the elastic and plastic properties of the material. The pile-up height is related to both the modulus over hardness ratio and the indenter shape and varies with strain rate and temperature.

Temperature has an effect on the pile-up of scratched PMMA. Cross-sectional profiles were performed at different positions along the scratch at different temperatures. There is a strong correlation between increased temperature and increased pile up height and modulus-to-hardness ratio Deformation is also strongly influenced by the type of sample material tested.

Figure 6:
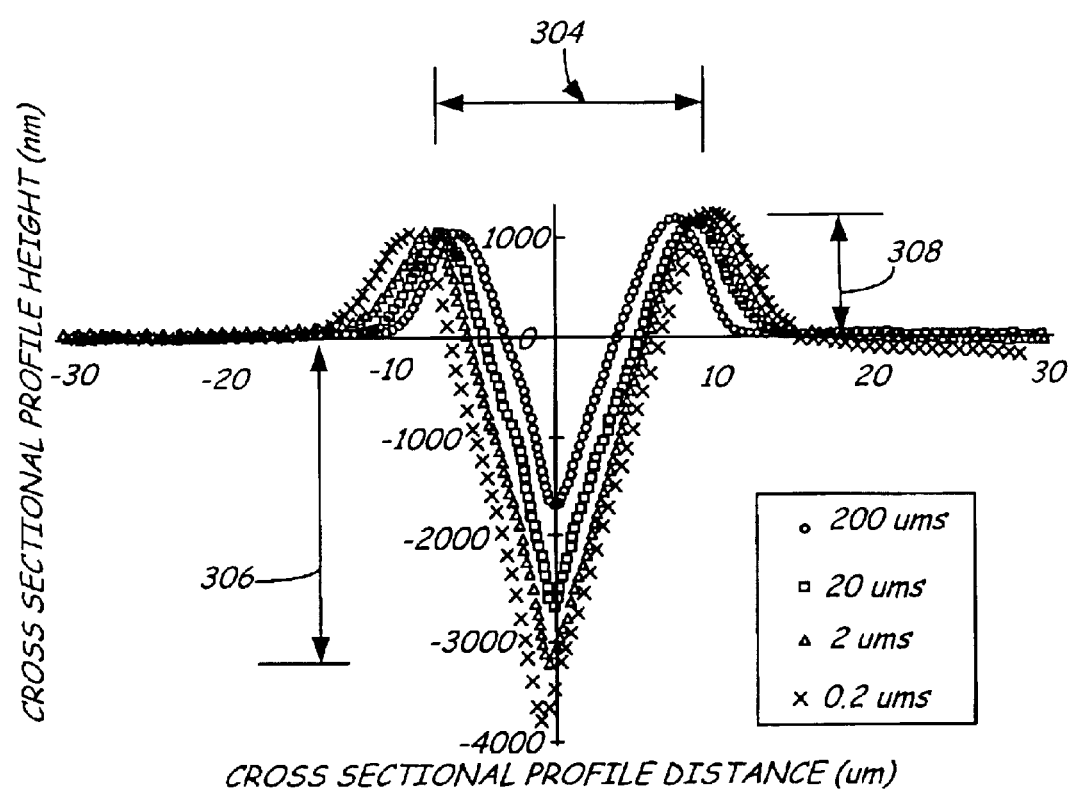
FIG. 6 shows cross-sectional profiles of grooves from scratch tests performed at various speeds.

The strain rate also has an effect on plastic deformation. Equation 8 shows that the strain rate varies with the scratch speed. In order to obtain a variation in the strain rate, the scratch speed was varied at room temperature. The shape of the groove was measured at the same position along the scratch (50 nN) and at different scratch speeds. FIG. 6 shows the results of these scratch tests performed at different speeds. Higher strain rates lead to smaller widths (indicated generally at 304) and depths (indicated generally at 306) of the groove. Surprisingly, the height (indicated generally at 308) of the pile-up apparently is not affected by the strain rate variations.

The parameter most commonly used to describe the ductile-to-brittle transition in scratch testing is the critical load. The dependence of the critical load on temperature when scratch tests are performed on PMMA. In general, fracture occurs at smaller loads for low temperatures and higher loads for high temperatures.

The morphology of the fracture also changes with varying temperature. Fracture is more extensive at low temperatures with a lot of missing material. In contrast, at high temperatures there is much less splintering on the sides of the groove and material seems to have plastically flowed. No fracture is present in front of the last position of the indenter because fracture occurs behind the contact point.

Temperature also affects steady state flow stress in that the flow stress decreases when temperature increases. However, regardless of temperature, the shape of the compression stress/strain curve is generally the same. The elastic modulus, which is the slope of the initial linear part of the curve, varies with temperature. Different strain rates have also been used to show that an increase in the strain rate increases the magnitude of the flow stress. Temperature has a tremendous effect on the shape of the tensile curves. At low temperatures, PMMA behaves like a brittle material with very little plasticity and breaks at very low strains and high stresses. At higher temperatures, PMMA behaves more like a rubber in which fracture occurs at high strains and lower stresses.

It is further known that yield stress $\Sigma_Y$ and fracture strength (stress required to cause brittle fracture) $\Sigma_B$ are both temperature dependent. Both the yield stress and fracture strength decrease with temperature, and there is a transition temperature where $\Sigma_Y=\Sigma_B$. Below this transition temperature, the yield stress is higher than the fracture stress and fracture dominates. Above the transition temperature, the situation is reversed leading to yielding and ductile behavior.

It is known that fracture during scratch testing can be due to tensile tearing. The very strong correlation between the tensile behavior of PMMA and the fracture behavior in scratch testing is known and leads to an explanation for the origin of fracture A compression zone is created ahead of the scratch where material in front of the scratch tip is compressed. Simultaneously, tensile stresses develop behind the scratch tip. If these stresses reach the fracture stress value of the material, then fracture would occur. This explanation is consistent with observations that fracture occurs behind the contact area and that the critical load exhibits the same "brittle-ductile" transition as in tensile tests.

Scratch deformation is also influenced by the geometry of scratch tips. Referring again back to FIG. 5, several important geometric parameters are shown. These parameter include radius R representing the spherical part of the tip indicated at 306 and a which is the half angle of the cone indicated at 308. The vertical height of the spherical part of the tip, $h_{sp}$, is indicated at 310 and can be calculated as:

$$h_{sp}=R(1-\sin\alpha) \quad \text{Equation 13}$$

At the height $h_{sp}$ the contact radius, $r_{hsp}$, indicated at 312 can be calculated as:

$$r_{hsp} = \sqrt[2]{R^2 - (R-h_{sp})^2} \quad \text{Equation 14}$$

More generally, at a given height d, indicated at 314, the contact radius, $r_c$, indicated at 316 can be expressed as:

$$\text{If } d < h_{sp} \quad r_c\sqrt[2]{R^2 - (r-d)^2} \quad \text{Equation 15}$$

$$\text{If } d > h_{sp} + (d - h_{sp})\tan\alpha \quad \text{Equation 16}$$

The strain rate influences both yield and fracture strengths $\sigma_Y$ and $\sigma_B$, for PMMA. When strain rate is increased, PMMA becomes more brittle. As discussed above, a commonly accepted equation for scratch strain rate is:

$$\varepsilon_s = \frac{V_{tip}}{a} \qquad \text{Equation 17}$$

which was assumed in the experiments and methods of the inventions.

The methods of the present invention were performed at room temperature to examine the influence of the scratch strain rate on the critical load first using a 90° cone with a 2 μm tip radius. In order to obtain a variation in the scratch strain rate, the scratch speed was changed for each scratch test. Scratch strain rate was calculated using Equation 8. The scratch speeds and corresponding strain rates are detailed in Table 3.

When the scratch strain rate increases for the 90° cone, the critical load decreases. This means that the PMMA fractures at smaller loads when the strain rate, or the scratch speed, is increased. Therefore, increasing the strain rate has the same effect as decreasing the temperature because increased strain rate reduces the critical load and makes the material behave in a more brittle fashion.

TABLE 3

Scratch strain rates corresponding to the scratch speed

| Speed | Strain rate |
|---|---|
| 200 μm/s | 15.0353 μm/μm/s |
| 20 μm/s | 1.2784 μm/μm/s |
| 2 μm/s | 0.1151 μm/μm/s |
| 0.2 μm/s | 0.0107 μm/μm/s |

The methods of the present inventions were also performed to determine strain rate dependence of the critical load for a 60° angle cone with a 4 μm tip radius. In this case, the strain rate dependence of the critical load is opposite than results observed for the 90° angle cone. In other words, critical load increases with the strain rate rather than decreases. These results suggest that the PMMA is more brittle at smaller strain rates. Therefore, according to these methods of the present inventions, the critical load itself cannot be used reliably to predict the fracture behavior of a material as a function of the strain rate. In carrying out these methods, one possibility considered was whether fracture in PMMA occurs when a critical deformation is reached.

Scratch tip geometry can influence the fracture behavior because it can influence contact deformation in the material.

The scratch tip geometry, for example a blunted cone, can be considered a composite shape that can be divided into a plurality of portions. In the case of a blunted cone, the two portions can comprise a spherical portion and a conical portion. However, other scratch tips, such as a blunted pyramidal scratch tip, can considered a composite expressed as spherical portion and a pyramid portion. It is noted, however, that the portion shapes and composite tip shapes are not limited to spheres, cones, and pyramids but can include, without limitation, other regular or irregular shapes where geometric portions can be combined to express a composite scratch tip shape.

It is known that spheres and cones impose totally different degrees of deformation and strain on sample material during scratch tests. The equivalent strain for a sliding contact between a sphere and a plane as can be expressed as:

$$\varepsilon_s = 0.2 \frac{r_c E}{R \sigma_Y} \qquad \text{Equation 18}$$

where $r_c$ is the contact radius, R is the sphere radius, E is the elastic modulus, $\sigma_Y$ is the yield stress, and $$\frac{E}{\sigma_Y}$$

is a constant. For the cone, the equivalent strain can be expressed as:

$$\varepsilon_C = 0.2 \cot\alpha \frac{E}{\sigma_Y} \qquad \text{Equation 19}$$

where α is the half angle of the cone. Before the methods of the present inventions were performed, it is believed that the deformation of a cone with a rounded tip had not been studied systematically.

The inventors assumed that if the total strain due to a scratch tip is a composite of the strains due to the two different geometric shapes, a mathematical model could be developed that to approximate the effect of the two geometries or portions.

In the present inventions, an exponential function $\epsilon_{Tot}$ has been developed comprising the sum of two other functions and is expressed as:

$$\epsilon_{Tot} = f(\epsilon_c) + g(\epsilon_s) \qquad \text{Equation 19.5}$$

where $f(\epsilon_s)$ and $g(\epsilon_c)$ are each fitting functions based on tip geometry. In the present example, $\epsilon_{Tot}$ represents the total deformation of the blunted cone and is a function of the strain due to the cone and strain due to the sphere.

Combining the effect of the two geometric shapes in the scratch tip, the approximation can be written as:

$$\epsilon_{Tot} = \lambda \epsilon_c (1 - e^{(-\theta r_c)}) + \gamma \epsilon_s e^{(-\beta r_c)} \qquad \text{Equation 20}$$

where, β, λ, γ, θ are fitting coefficients, and $\epsilon_s$, $\epsilon_c$ are, respectively, the deformation due to a sphere and the deformation due to a cone. Equation 20 is a way to interpolate between the fitting functions representing two different behaviors caused by the two geometric shapes in the scratch tip.

Figure 7:
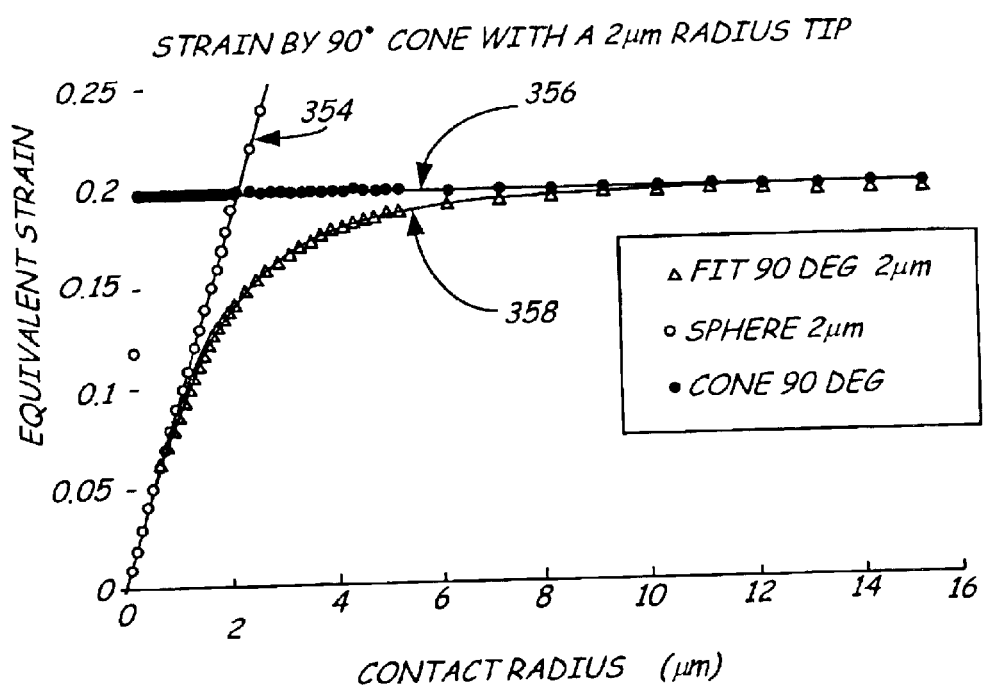
FIG. 7 shows plots of asymptotes and fitting function for a 90' cone with 2 $\mu$m radius.

FIG. 7 illustrates the results of a scratch test performed with a 90° cone having a tip radius of 2 μm radius. Asymptotes 354 and 356 represent the two limiting behaviors, respectively, of the sphere deformation for small contact radii and the cone deformation for larger contact radii.

In other words, the two asymptotes 354, 356 represent the strain produced by a pure cone and a pure sphere. Note that the strain is caused by a cone is constant whatever the contact radius is. For the sphere, the strain increases with the contact radius. The exponential curve 358 shows the approximation from equation 20 of the total strain generated by the 90 cone with a 2 μm radius.

Figure 8:
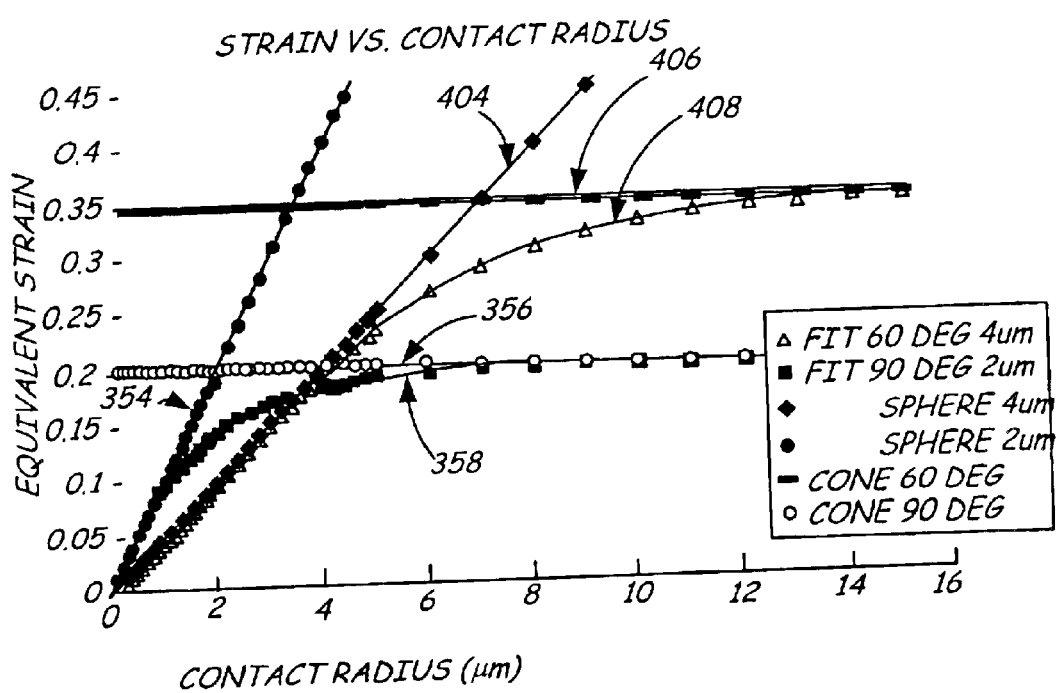
FIG. 8 shows plots of asymptotes and fitting functions for a 90' cone with 2 $\mu$m radius and a 600 cone with 4 $\mu$m radius.

FIG. 8 shows results of modeling by applying Equation 20 for both the 90 cone with a 2 μm tip radius and the 60 cone with a 4 μm radius. For a 60 cone with a 4 μm radius, asymptotes 404, 406 are the fitting functions for curve 408 generated from equation 20.

When comparing asymptotes 354, 356, discussed previously, to asymptotes 404, 406, it is clear that for the same contact radius, the deformation caused by the two different scratch tips is significantly different. This observation suggested that it would be important to consider the depth at which the fracture occurs during scratching, as a function of the scratch speed. Results are shown in Table 4.

Table 4 shows that for both scratch tips, the critical depth decreases as the scratch speed increases. Since the relationship between the contact radius $r_c$ indicated as 316 and the depth d indicated as 314 on FIG. 5, by applying Equations 15 and 16, the critical depth can be converted to a critical contact radius.

Figure 9:
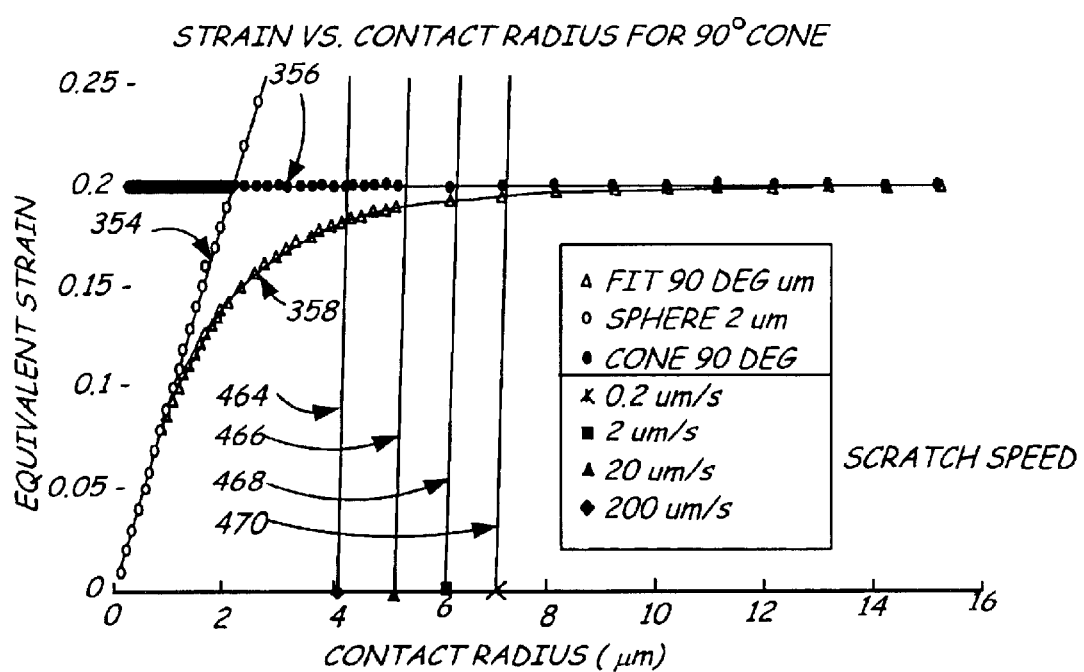
FIG. 9 shows plots of asymptotes and fitting function for a 90° cone with 2 $\mu$m radius and vertical plots of critical radii at various speeds to indicate critical strain.
Figure 10:
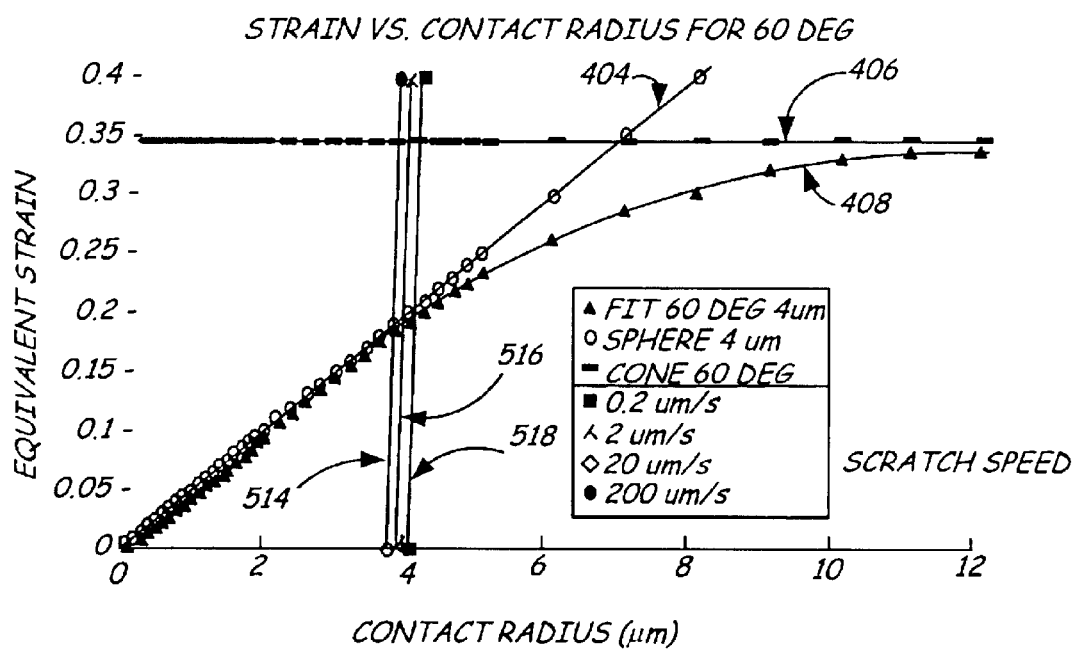
FIG. 10 shows plots of asymptotes and fitting function for a 60° cone with 4 $\mu$m radius and vertical plots of critical radii at various speeds to indicate critical strain.

FIGS. 9 and 10 shown curve 358 and curve 408, respectively, previously shown on FIG. 8. However, values of critical contact radius are shown as vertical lines 464, 466, 468, 470 in FIG. 9. Similarly, vertical lines 514, 516, 518 are shown in FIG. 10 also representing values for critical contact radius. The intersections between vertical lines 464, 466, 468, 470 with curve 358 and between vertical lines 514, 516, 518 with curve 408 gives the equivalent strain or deformation at fracture.

For the cases of the 90° cone shown in FIG. 9, it is noteworthy that fracture occurs at a depth that reaches the conical part of the scratch tip. The deformation at fracture is thus more due to a cone than to a sphere. Moreover, this is true at all scratch speeds.

For the 60° cone shown in FIG. 10, fractures occur in the spherical part of the scratch tip well before the transition to the cone. It is also noteworthy that the different scratch speeds generate fracture over a smaller range of strain than for the 90° cone. This is because strain increases rapidly as a function of contact radius for the sphere but remains constant for the cone.

The two plots in FIGS. 9 and 10 can be used to determine the strain at the fracture point for the different scratch speeds. Results are presented in Table 5 and Table 6. It should be noted that as used herein "plot" refers generally to a method of analysis. As appreciated by those skilled in the art, other forms of analysis to achieve the same result or conclusion can be accomplished using other techniques that do not include plotting.

Knowing the critical contact radius and the scratch speed, one can calculate the "critical strain rate", at which the fracture occurs as follows:

$$\varepsilon_{Critical} = \frac{V_{tip}}{r_{c_{critical}}} \qquad \text{Equation 21}$$

Results for the critical strain rate are also presented in Table 5 and Table 6.

Figure 11:
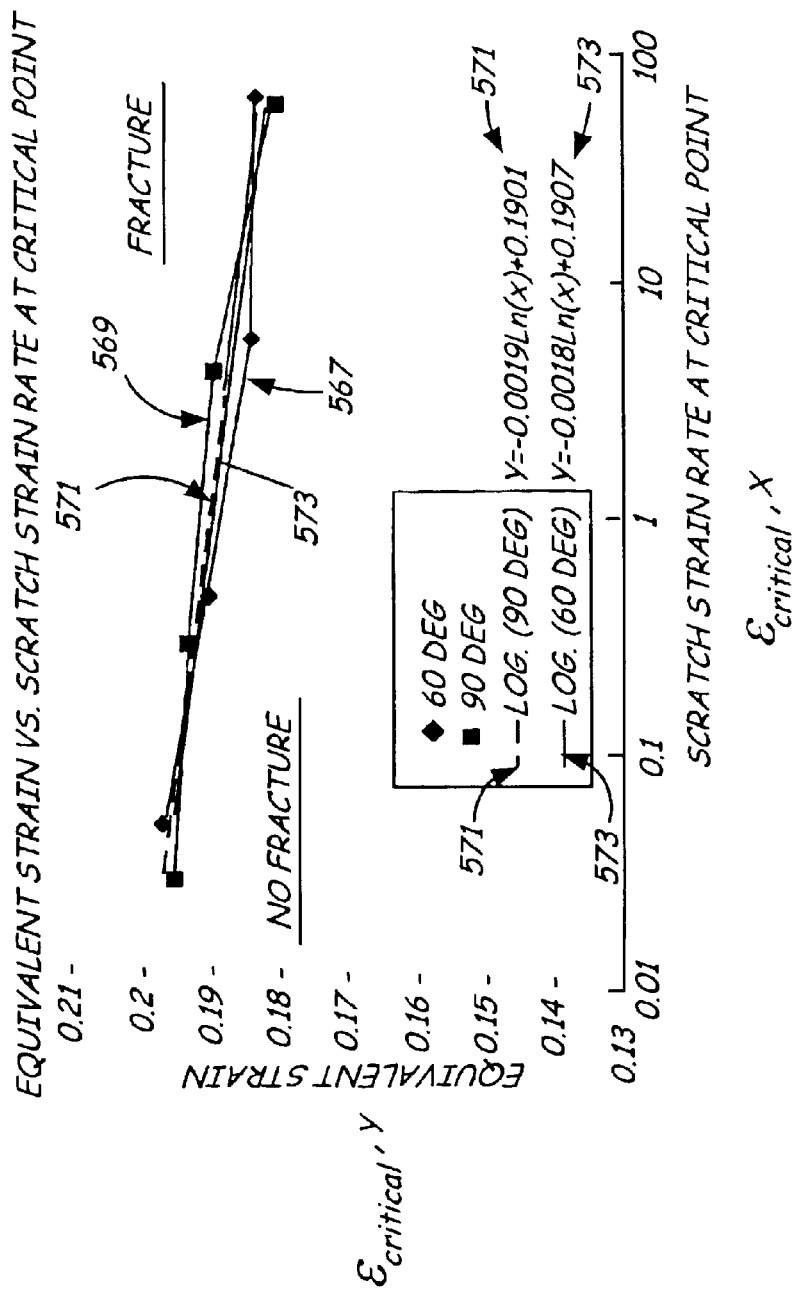
FIG. 11 shows plots of equivalent strain versus critical scratch strain rate with fracture and non-fracture regions and fitting log functions for the two blunted cones.

FIG. 11 shows a plot 567, 569 for critical deformation strain as a function of critical strain rate using the results in Table 5 and Table 6 for both the 90° cone and the 60° cone, respectively.

For both scratch tips, the two plots 567, 569 are very similar and exhibit the same trends. In order to compare the two plots 567, 569 they have been approximated ith with fitting log functions 571 for the 90° cone and 573 for the 60° cone. The two log functions 571, 573 resulted in very similar equations:

For the 60 cone:

$$y=-0.0018\mathrm{Ln}(x)+0.1907 \qquad \text{Equation 22}$$

For the 90 cone:

$$y=-0.0019\mathrm{Ln}(x)+0.1901 \qquad \text{Equation 23}$$

TABLE 5

Critical values for the 60° cone

| Speed $\mu$m/s | Critical load mN | Critical depth $\mu$m | Critical contact radius $\mu$m | Equivalent Strain at fracture $\mu$m/$\mu$m | Critical strain rate $\mu$m/$\mu$m/s |
|---|---|---|---|---|---|
| 0.2 | 18.362 | 3.070 | 4.082 | 1696.94E−4 | 0.046 |
| 2 | 19.493 | 2.806 | 3.929 | 1905.23E−4 | 0.508 |
| 20 | 20.903 | 2.584 | 3.801 | 1849.43E−4 | 5.261 |
| 200 | 23.223 | 2.555 | 3.784 | 1842.06E−4 | 52.845 |

TABLE 6

Critical values for the 90° Cone

| Speed $\mu$m/s | Critical load mN | Critical depth $\mu$m | Critical contact radius $\mu$m | Equivalent strain at fracture $\mu$m/$\mu$m | Critical strain rate $\mu$m/$\mu$m/s |
|---|---|---|---|---|---|
| 0.2 | 51.4 | 6.255 | 7.083 | 1958.71E−4 | 0.028 |
| 2 | 45.906 | 5.326 | 6.154 | 1936.81E−3 | 0.325 |
| 20 | 40.16 | 4.348 | 5.177 | 1898.80E−4 | 3.863 |
| 200 | 30.30 | 3.247 | 4.075 | 1822.16E−4 | 49.068 |

Figure 12:
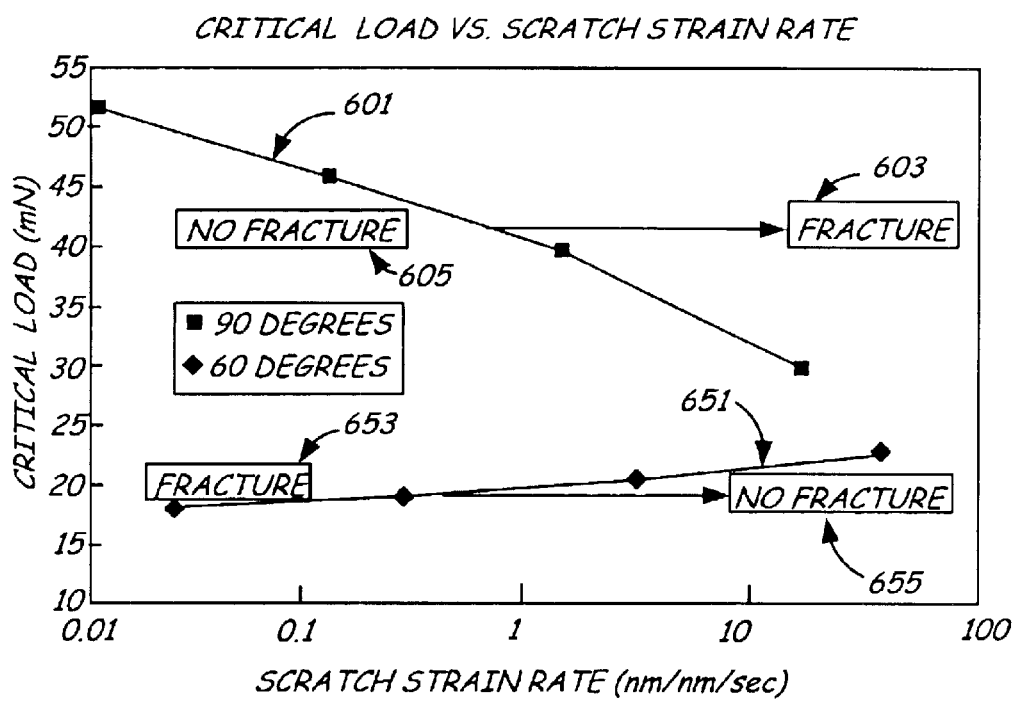
FIG. 12 shows plots of critical load versus scratch strain rate with fracture and non-fracture regions for the two blunted cones.

It was very important for the methods of the present inventions that these the results for critical strain do not depend upon the tip geometry and can therefore be considered as material properties much in the same manner as the hardness or the modulus. Furthermore, FIG. 12 plots critical load versus strain rate and shows the different behavior of the two scratch tips. Curve 601 for a 90° cone shows critical load decreasing as strain rate increases. In contrast, curve 651 for a 60° cone shows increasing critical load with increasing strain rate. For both curves 601 and 651, the region above the curve represents the region where the material fractures Therefore, for a 90° cone, the sample material fractures in region 603 but does not fracture in region 605. Similarly, for a 60° cone, the material fractures in region 653 but does not in region 655. Thus, equivalent strain at fracture changes with strain rate at a constant load. According to the strain rate definition given in Equation 8, an increase in strain rate also means a decrease in contact radius. Referring back to FIGS. 9 and 10, the same variation in contact radius generates a larger change in equivalent strain for the 600 cone than for the 90° cone. In the case of the 90° cone, the change in strain is small.

The results of experiments can be used to characterize an unknown material or to predict when the fracture during scratching will occur for a given material for which some properties are known.

For an Unknown Material

Figure 13:
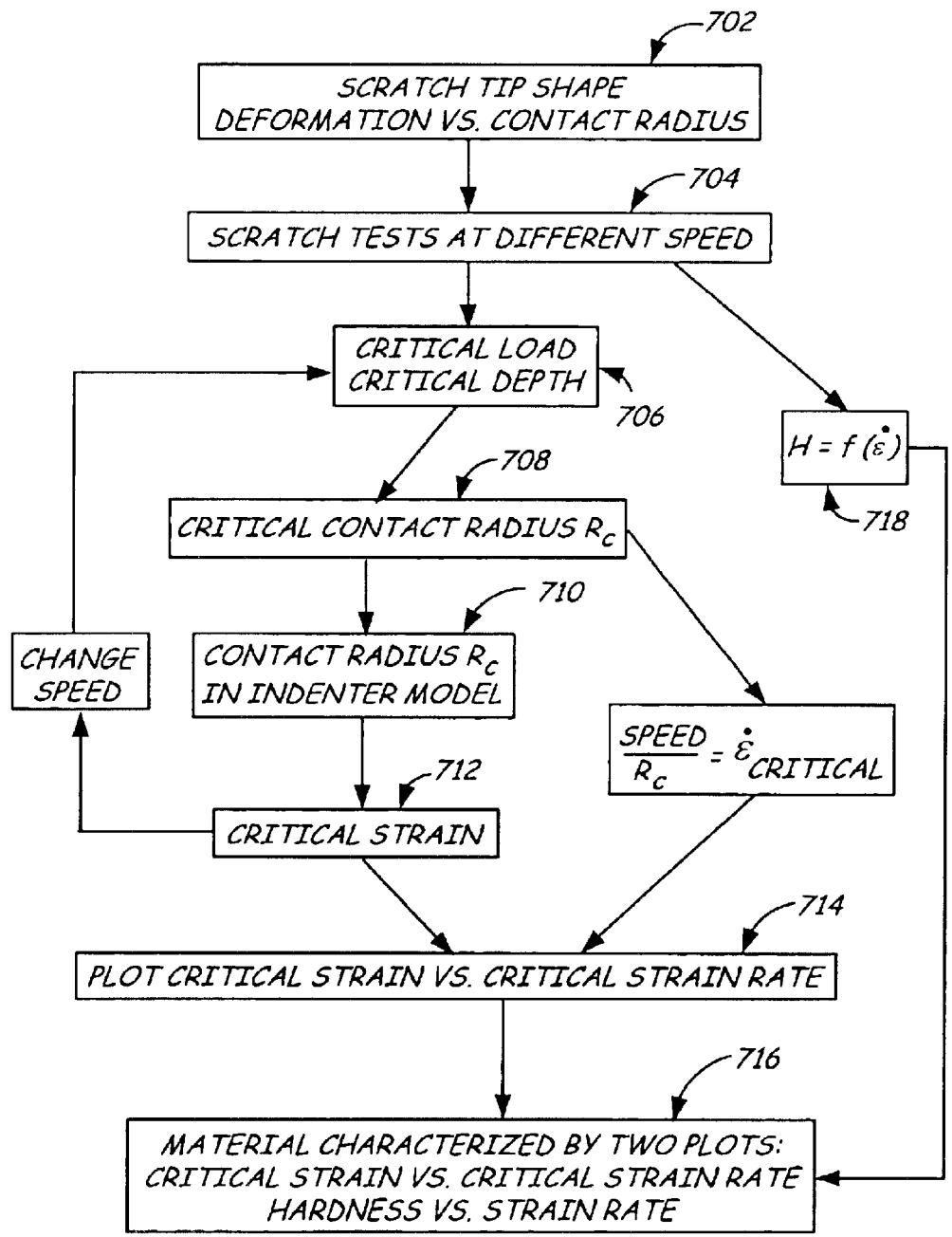
FIG. 13 is a flowchart of a method where the test sample material has unknown mechanical properties.

A method is illustrated by flowchart in FIG. 13 where the sample material is unknown. At step 702, the scratch tip geometry is selected and at step 704, scratches are made on the sample material at different speeds. At step 706, critical load and critical depth is measured for each test. At step 708, Equation 15 or Equation 16 is employed to calculate the critical contact radius from the critical depth. Then, at step 710, the critical contact radius is used to determine the critical strain rate by means of Equation 21. At step 712, the critical strain is calculated with the deformation approximation represented by Equation 20.

At step 714, a plot can be developed and critical strain can be plotted as a function of the critical strain rate similar to the plot in FIG. 11. Such a plot can be considered at step 716 as fundamental to material behavior, and importantly, independent of scratch tip geometry. Further, at step 718, another material behavior that can be obtained which is contact pressure or scratch hardness as a function or, on the scratch strain rate.

For a Material with a Known Scratch Behavior

Figure 14:
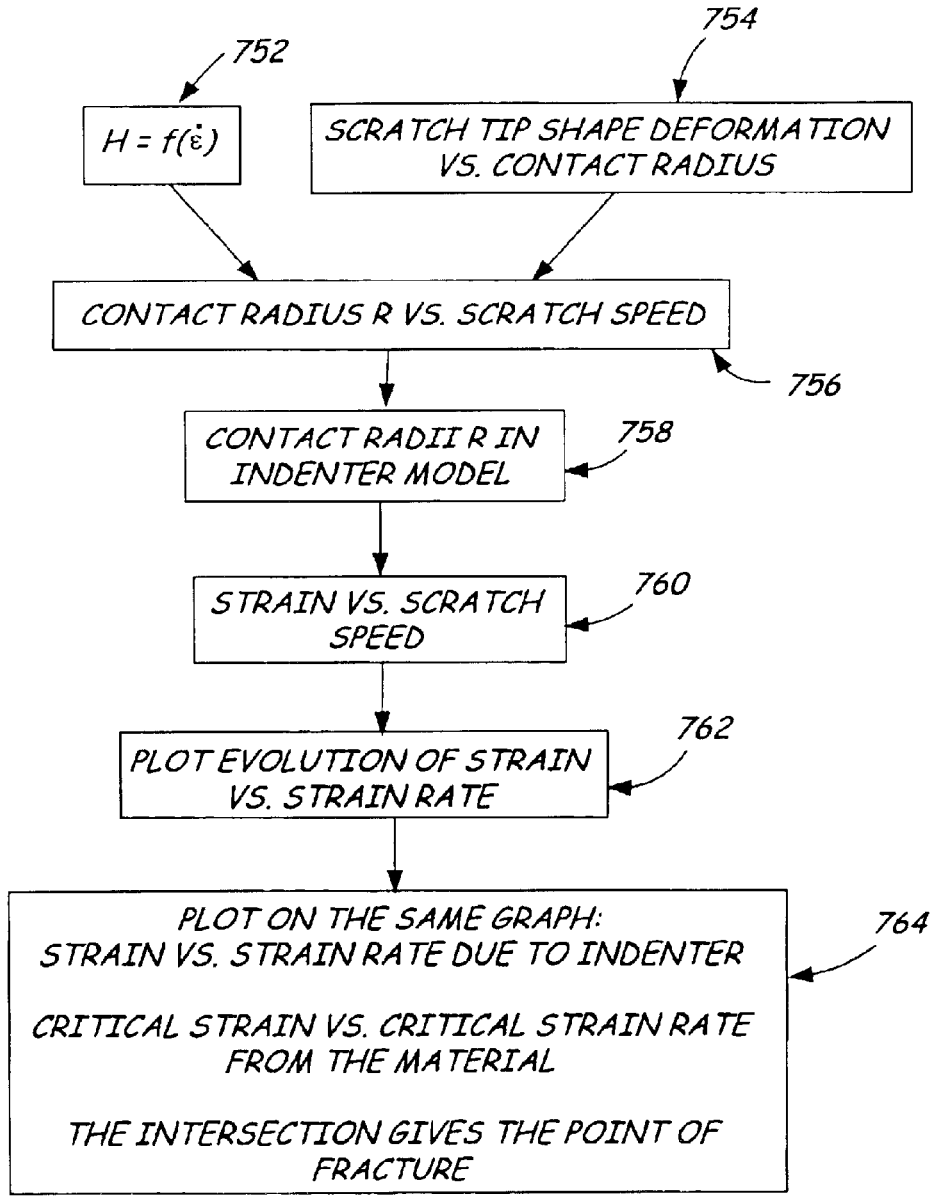
FIG. 14 is a flowchart of a method where the test sample material has known mechanical properties.
Figure 15:
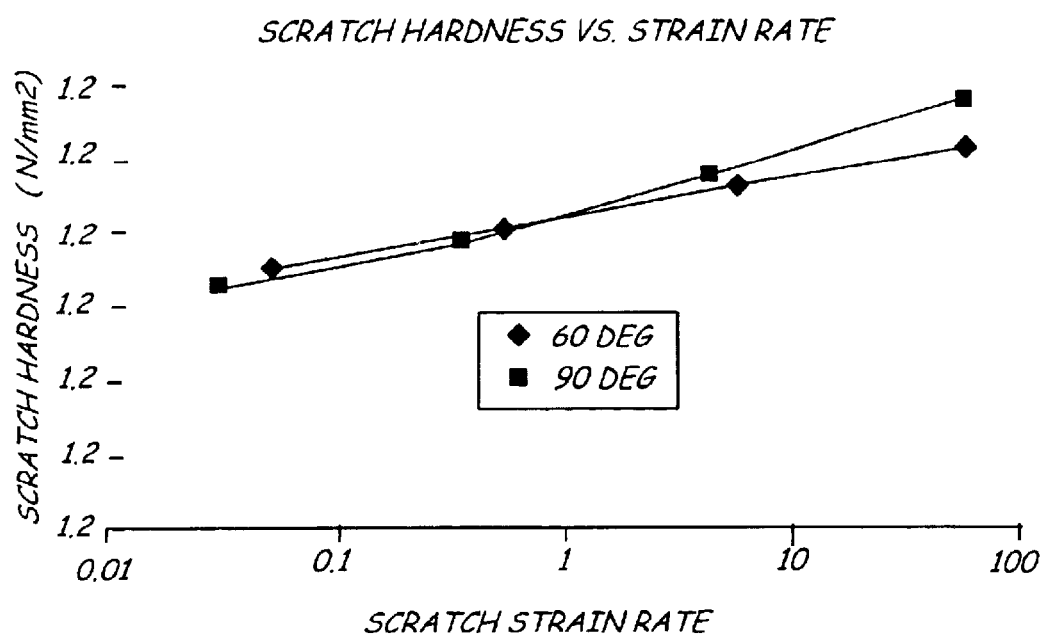
FIG. 15 shows plots of scratch hardness versus scratch strain rate for the two blunted cones.

In the case of a material with known scratch behavior, a method is presented as a flowchart in FIG. 14. At step 752 scratch hardness vs. strain rate, or $H_s=f(\epsilon)$ is plotted as illustrated in FIG. 15. At step 754, critical strain vs. critical strain rate is plotted as illustrated in FIG. 11. Step 752 and Step 754 can be accomplished because the scratch behavior for the material is known. Also, at step 754, the geometry of the scratch tip is selected and/or known.

Then at step 756, from the scratch tip geometry and the plot $H_s=f(\epsilon)$, the contact radius can be calculated at each point as a function of the strain rate and then, as a function of the scratch speed. At step 758, the contact radius can be plotted on a graph of equivalent strain vs. contact radius, which is obtained from the indenter geometry. At step 760, the equivalent strain can be extracted from this last graph and plotted as a function of scratch speed. At step 762, with known values for the contact radius, the equivalent strain and the scratch speed, deformation can be plotted as a function of the strain rate. Then, at step 764, the intersection between critical strain vs. critical strain rate and strain vs. strain rate gives the point of fracture.

Figure 16:
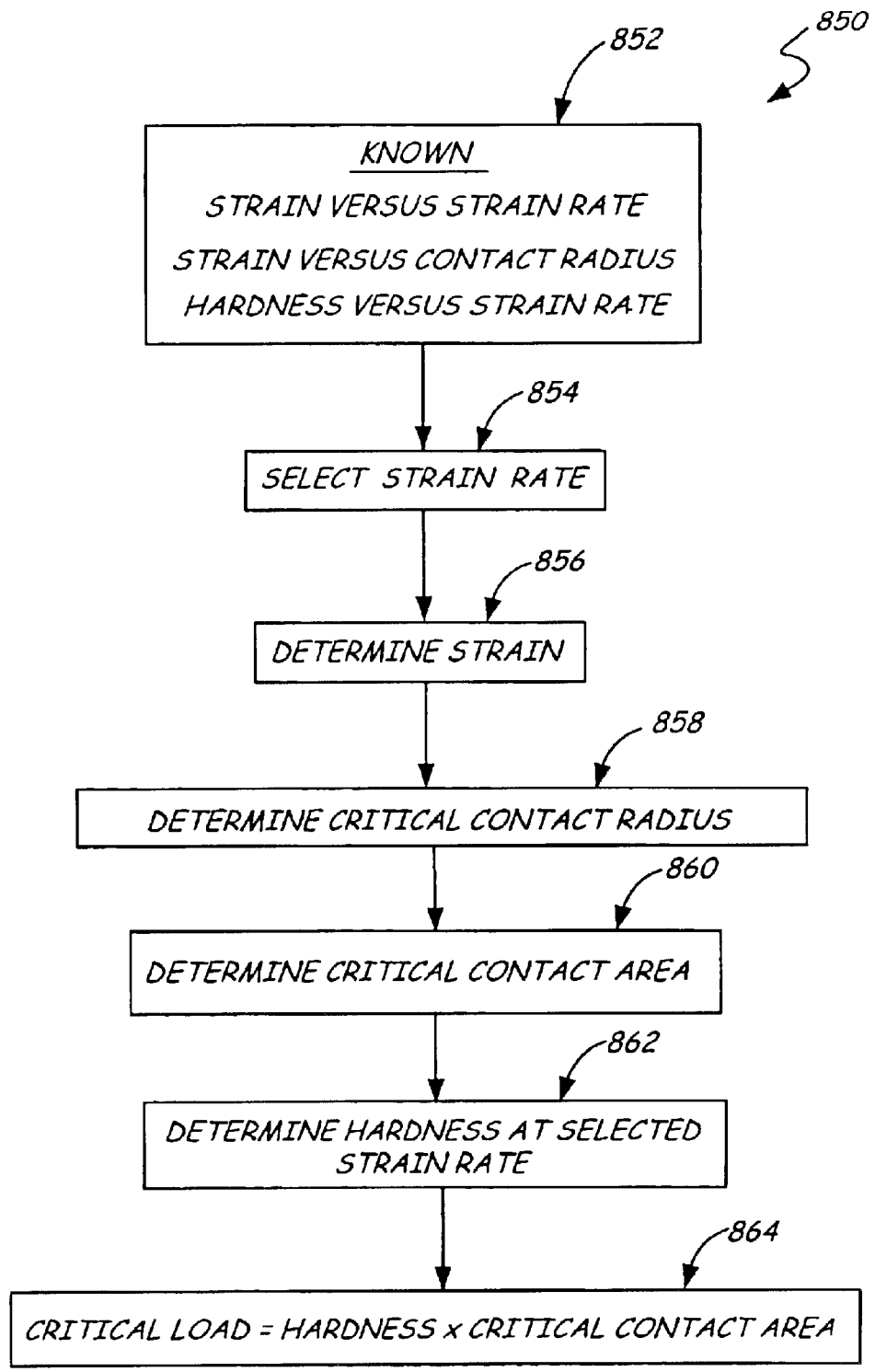
FIG. 16 is a flow chart of a method of determining critical load.

In other words, a critical load at selected strain rates can be determined from the results generated by the analysis or plot generated from equation 20 and from other equations presented in the description above. FIG. 16 shows a flowchart 850 of a method of determining critical load.

At step 852, assume that the material is known, then the results plotting strain as a function of strain rate similar to results presented in FIG. 11 are known. Also known are the results for strain as a function of contact radius similar to those plotted in FIGS. 9 and 10 (from equation 20) but for a selected scratch tip geometry. Finally, the results of hardness as a function of strain rate similar to results presented in FIG. 15 are known.

At step 854 a strain rate is selected to be studied. At step 856, from the plot of strain versus strain rate at the critical point, such as shown in FIG. 11, the strain at the selected critical strain rate can be determined. At step 858, from this critical strain and from using equation 20 or results similar to those on FIGS. 9 and 10, critical contact radius can be determined readily.

At step 860, once the critical contact radius is known then contact area $A_N$ can be readily determined based on tip geometry similar to equation 2. At step 862, hardness is determined at the selected strain rate. At step 864, since both $A_N$ and hardness has been determined, then because $HA_N=$ critical load (see equation 1), the critical load can be determined. It is noted that the critical load has been determined as a function of the studied strain rate discussed above.

Although the present invention has been described with reference to preferred embodiments, workers skilled in the art will recognize that changes may be made in form and detail without departing from the spirit and scope of the invention.

What is claimed is:

1. A method of determining properties of an unknown test material by scratch testing, comprising the steps of:
    applying a load over a surface of a test sample using a scratch tip having a composite shape comprising a selected plurality of geometric parameters at a selected speed to form a groove;
    measuring a critical depth of the groove and the critical load applied; and
    analyzing a critical strain of the test sample as a function of the plurality of geometric parameters, the critical depth, and the critical load.

2. The method of claim 1 and further comprising calculating a critical strain rate.

3. The method of claim 2 and further comprising repeating the steps of applying, measuring, and calculating for a different selected speed.

4. The method of claim 2 comprising analyzing strain as a function of critical strain rate.

5. The method of claim 2 further comprising calculating test material hardness as a function of critical strain rate.

6. The method of claim 1 further comprising the step of calculating critical radius as a function of the critical depth.

7. The method of claim 1, wherein the combination shape comprises a cone with a rounded tip, and the geometric parameters comprise a sphere radius and a cone angle.

8. The method of claim 1, wherein the combination shape comprises a pyramid with a rounded tip.

9. A method of determining properties of an unknown test material by scratch testing, comprising the steps of:
    applying a load over a surface of a test sample using a scratch tip having selected geometric parameters at a selected speed to form a groove;
    measuring a critical depth of the groove and the critical load applied;
    analyzing a critical strain of the test sample as a function of the geometric parameters, the critical depth, and the critical load; and
    calculating critical radius as a function of the critical depth, wherein the critical strain $\epsilon_{tot}$ is approximately equal to $\lambda\epsilon_c(1-e^{(-\theta r_c)})+\gamma\epsilon_s e^{(-\beta r_c)}$, wherein $r_c$ is the critical radius, $\lambda$, $\theta$, $\beta$, and $\gamma$ are fitting coefficients and $\epsilon_s$ and $\epsilon_c$ are strains due to a plurality of geometric shapes, respectively, having the selected geometric parameters.

10. The method of claim 9 wherein the geometric shapes comprise a sphere and a cone.

11. A method of determining properties of an unknown test material by scratch testing, comprising the steps of:
    applying a load over a surface of a test sample using a scratch tip having selected geometric parameters at a selected speed to form a groove;
    measuring a critical depth of the groove and the critical load applied;
    analyzing a critical strain of the test sample as a function of the geometric parameters, the critical depth, and the critical load; and
    calculating a critical strain rate, wherein the critical strain rate is equal to the speed of the scratch tip divided by a width of the groove.

12. A method of determining properties of an unknown test material by scratch testing, comprising the steps of:
    applying a load to a surface of a test sample using a scratch tip having a selected composite shape described with geometric parameters at a selected speed over the sample surface to form a groove;
    measuring a critical depth of the groove and the critical load applied; and
    approximating a critical strain of the test sample based on at least the geometric parameters of the scratch tip.

13. The method of claim 12, wherein approximating a critical strain comprises approximating a critical strain of the test sample based on the geometric parameters comprising a sphere radius and at least one other geometric parameter.

14. The method of claim 13, wherein the at least one other geometric parameter comprises one of a cone angle and a pyramidal parameter.

* * * * *